US00PP29546P2

(12) United States Plant Patent
Hartman

(10) Patent No.: US PP29,546 P2
(45) Date of Patent: Jul. 24, 2018

(54) ***CALADIUM* PLANT NAMED 'CARIBBEAN CORAL'**

(50) Latin Name: *Caladium X hortulanum*
Varietal Denomination: Caribbean Coral

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 15/530,470

(22) Filed: Jan. 18, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Caladium* plant named 'Caribbean Coral', characterized by its intermediate height and upright plant habit; leaf petioles that are upright to outwardly leaning with development; vigorous growth habit and rapid growth rate; strap (or lance) type leaves that are dark olive green in color with dark pink-colored venation surrounded with lighter pink areas and interveinal areas that are pink variably suffused with green in color with random greenish white and pink-colored spots; and petioles that are light green in color, distally tinged with pink and tan peak and tan green, and overall with brown-colored streaks, stipples and tessellations.

4 Drawing Sheets

Botanical designation: *Caladium X hortulanum.*
Cultivar denomination: 'CARIBBEAN CORAL'.

BACKGROUND OF THE INVENTION

The present invention relates to a new and distinct cultivar of *Caladium* plant, botanically known as *Caladium X hortulanum*, commercially referred to as a strap (or lance) leaf-type *Caladium* and hereinafter referred to by the name 'Caribbean Coral'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium X hortulanum* 'John Peed', not patented, as the female, or seed, parent with *Caladium X hortulanum* 'White Marble', disclosed in U.S. Plant Pat. No. 18,819, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Caribbean Coral'. These characteristics in combination distinguish 'Caribbean Coral' as a new and distinct *Caladium* plant:

1. Intermediate in height and upright plant habit; leaf petioles upright to outwardly leaning with development.
2. Vigorous growth habit and rapid growth rate.
3. Strap (or lance) type leaves that are dark olive green in color with dark pink-colored venation surrounded with lighter pink areas and interveinal areas that are pink variably suffused with green in color with random greenish white and pink-colored spots.
4. Petioles that are light green in color, distally tinged with pink and tan peak and tan green, and overall with brown-colored streaks, stipples and tessellations.

Plants of the new *Caladium* differ primarily from plants of the female parent, 'John Peed', in the following characteristics:

1. Plants of the new *Caladium* have strap (or lance) type leaves whereas plants of 'John Peed' have fancy type leaves.
2. Plants of the new *Caladium* and 'John Peed' differ in leaf color as leaves of 'John Peed' have dark red-colored centers and red-colored venation with dark green-colored margins.
3. Plants of the new *Caladium* and 'John Peed' differ in leaf petiole color as leaf petioles of 'John Peed' are dark pink in color with dark green to almost black-colored stipples and streaks.

Plants of the new *Caladium* differ primarily from plants of the male parent, 'White Marble', in the following characteristics:

1. Plants of the new *Caladium* and 'White Marble' differ in leaf color as leaves of 'White Marble' are dark green in color with white-colored venation and areas surrounding the veins with greenish white-colored interveinal areas.
2. Plants of the new *Caladium* and 'White Marble' differ in leaf petiole color as leaf petioles of 'White Marble' are tan green in color with darker green stipples and streaks.

Plants of the new *Caladium* can be compared to plants of *Caladium X hortulanum* 'Scarlet Flame', disclosed in U.S. Plant Pat. No. 25,419. In side-by-side comparisons, plants of the new *Caladium* differ primarily from plants of 'Scarlet Flame' in the following characteristics:

1. Plants of the new *Caladium* are taller and more upright than and not as mounding as plants of 'Scarlet Flame'.
2. Plants of the new *Caladium* and 'Scarlet Flame' differ in leaf color as leaves of 'Scarlet Flame' are dark green in color with rose red-colored venation and pink and rose red-colored spots and blotches.
3. Plants of the new *Caladium* and 'Scarlet Flame' differ in leaf petiole color as leaf petioles of 'Scarlet Flame' are distally flushed with pink with close to black-colored streaks and stripes.

Plants of the new *Caladium* can be compared to plants of *Caladium X hortulanum* 'Lance Whorton', not patented. In side-by-side comparisons, plants of the new *Caladium* differ primarily from plants of 'Lance Whorton' in the following characteristics:

1. Plants of the new *Caladium* are slightly shorter and denser than plants of 'Lance Whorton'.
2. Plants of the new *Caladium* and 'Lance Whorton' differ in leaf color as leaves of 'Lance Whorton' are dark green in color with rose red venation and red to rose pink-colored areas surrounding the veins with pinkish green-colored interveinal areas and random pinkish orange-colored spots.
3. Plants of the new *Caladium* and 'Lance Whorton' differ in leaf petiole color as leaf petioles of 'Lance Whorton' are tan pink in color with darker-colored streaks, stipples and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Caribbean Coral' in a container and grown in a shadehouse (tuber not de-eyed).

The photograph at the top of the second sheet is a comparison view of typical potted plants of the female parent, 'John Peed' (left), 'Caribbean Coral' (center) and the male parent, 'White Marble' (right).

The photograph at the bottom of the second sheet is a comparison view of typical potted plants of 'Scarlet Flame' (left), 'Caribbean Coral' (center) and 'Lance Whorton' (right).

The photograph at the top of the third sheet is a side perspective view of typical plants of 'Caribbean Coral' grown in an open field.

The photograph at the bottom of the third sheet is a comparison view of typical plants of 'Caribbean Coral' grown in containers; the plant on the left has not had its tuber de-eyed and the plant on the right has had its tuber de-eyed prior to planting.

The photograph at the top of the fourth sheet is a close-up view of typical freshly-harvested tubers with roots and leaf petioles of 'Caribbean Coral'.

The photograph at the bottom of the fourth sheet is a close-up view of a typical inflorescence of 'Caribbean Coral'.

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were six weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium X hortulanum* 'Caribbean Coral'.

Parentage:

*Female, or seed, parent.*—*Caladium X hortulanum* 'John Peed', not patented.

*Male, or pollen, parent.*—*Caladium X hortulanum* 'White Marble', disclosed in U.S. Plant Pat. No. 18,819.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic to ovate in shape. Height: About 2 cm. Diameter: About 2.5 cm to 4 cm. Segment height: About 1.4 cm to 2 cm. Segment diameter: About 1.7 cm to 2 cm. Texture: Thick, starchy; somewhat brittle. Color: Epidermis, freshly-harvested: Close to 199B and N199B. Epidermis, dried: Close to 200A to 200B. Cortical tissue: Close to 2D. Axillary buds: Close to N155D and N155C. Root description:

Thick, fleshy contractile roots with few lateral branches; color, close to N155D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height and upright plant habit; vigorous growth habit and rapid growth rate; potted plants in finished or saleable form in about six weeks after planting tubers; leaf petioles and leaves arise from one or more growing points on tubers; petioles mostly upright and outwardly leaning with development; inflorescences held at the foliar plane on strong upright scapes.

*Plant height, from soil level to top of foliar plane, shadehouse-grown potted plants*.—About 32 cm to 38.9 cm.

*Plant height, from soil level to top of inflorescences, shadehouse-grown potted plants*.—About 39 cm.

*Plant diameter or spread, shadehouse-grown potted plants*.—About 48 cm to 56 cm.

*Number of shoots per plant, shadehouse-grown potted plants, tubers not de-eyed*.—About two to three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 4.4 cm to 9.2 cm. Width: About 1.3 cm to 1.7 cm. Shape: Wedge-shaped or ligulate. Apex: Acuminate, cuspidate. Base: Sheathing the stem. Color, inner surface: Close to N155B and 196D; colors and patterns on the outer surface are visible on the inner surface. Color, outer surface: Close to N170D and 36D; tinged with close to 147D and variably streaked and stippled with close to 200B; with development, color becoming closer to 199B faintly tinged with close to 187C.

Leaf description:

*Arrangement and type*.—Alternate; simple; strap (or lance)-type.

*Length, shadehouse-grown potted plants*.—About 17 cm to 22.5 cm.

*Width, shadehouse-grown potted plants*.—About 9.5 cm to 13.5 cm; when flattened, about 10.4 cm to 14.7 cm.

*Blade aspect*.—Mostly flat or somewhat cupped in the center.

*Shape*.—Ovate with lanceolate tendencies.

*Apex*.—Acuminate.

*Base*.—Sagittate to peltate.

*Margin*.—Entire; wavy with broad undulations.

*Texture, upper and lower surfaces*.—Smooth, glabrous; leathery.

*Luster, upper surface*.—Dull sheen.

*Luster, lower surface*.—Glaucous, dull sheen.

*Venation pattern*.—Pinnate.

*Color, shadehouse-grown potted plants*.—Developing and fully expanded leaves, upper surface: Background color: Close to 147A tinged with close to N189A. Margins: Close to 147A tinged with close to N189A; at the edge, close to 187A. Towards the margins: Close to 51B, 51C, 147A and 137A. Basal notch: Close to 187B. Midvein and primary venation: Darker than 53D and close to 53D tinged with close to 185B; proximally, veins may be streaked with close to 147C and 147B. Areas surrounding venation: Close to 51D or close to 51B and 51C randomly tinged and mottled with close to 137A and 147A. Interveinal areas: Close to 51B and 51C randomly tinged and mottled with close to 137A and 147A. Random spots: Close to 155B, 155D and 49D, Developing and fully expanded leaves, lower surface: Background color: Close to 191A tinged with close to 189A. Margins: Close to 191A tinged with close to 189A; at the edge, close to 187A. Towards the margins: Close to 191A tinged with close to 189A, 147C, 181C, 181D, 50C and 50D. Basal notch: Close to 187A. Midvein and primary venation: Close to 147D and 194C with streaks and flecks, close to 182B and 182C. Secondary venation: Close to 48B to 48C and 148B. Interveinal areas: Close to 50C, 50D, 147B and 147C. Random spots: Close to 155C and 36D.

*Petioles*.—Aspect: Initially upright and straight; with development, somewhat outwardly leaning; flexible. Length, shadehouse-grown potted plants: About 27.6 cm to 34.5 cm. Diameter, distally, shadehouse-grown potted plants: About 4 mm to 5 mm. Diameter, proximally, shadehouse-grown potted plants: About 6 mm to 8.5 mm. Texture: Smooth, glabrous. Color, shadehouse-grown potted plants: Close to 182C, 182D and 199D densely streaked, stippled and tessellated with close to 147A tinged with close to 200A and 200B; below the leaf and petiole junction, close to 147B and 147C variably tinged with close to 182D and sparsely streaked with close to 182A. Wing length, shadehouse-grown potted plants: About 5 cm to 8 cm. Wing diameter, shadehouse-grown potted plants: About 5 mm to 8 mm. Texture and luster, inner and outer surfaces: Smooth, glabrous; dull. Wing color, shadehouse-grown potted plants: Inner surface: Close to 155B to 155C and 196D; colors and patterns on the outer surface are visible on the inner surface. Outer surface: Close to N170D and 36D tinged with close to 147B and 147C and stippled and streaked with close to 200B tinged with close to 147A to 147B.

Inflorescence description: Inflorescences observed on seven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring in central Florida; flowers develop about seven weeks after growth commences; inflorescences last about three days before fading; inflorescences persistent.

*Spathe*.—Length, overall: About 11.8 cm. Length, distal open portion: About 8.6 cm. Length, proximal closed portion: About 3.2 cm. Width, distal open portion: About 3.1 cm. Depth, distal open portion: About 2.4 cm. Width, at constriction: About 1.2 cm. Width, proximal closed portion: About 2.2 cm. Shape, open portion: Narrowly elliptic. Apex: Acuminate. Base: Acute. Margin: Entire. Texture, front and rear surfaces: Smooth, glabrous. Luster, front surface: Dull sheen. Luster, rear surface: Dull sheen; proximally, glaucous. Color, front surface: Distal open portion: Close to 145D and 155C; with development, color becoming closer to 199C to 199D. Proximal closed portion: Close to 194A and 147C; proximally flushed with close to N186D and 187A; color does not change with development. Color, rear surface: Distal open portion: Close to 145C and 145D, central area, tinged with close to 145B; distally, random spots, close to 155B; color does not change with development. Proximal closed portion: Close to 147B, 147C and 147D mottled and flecked with close to 148C and 148D; color does not change with development.

*Spadix*.—Length, overall: About 8.5 cm. Length, male flower zone: About 5.1 cm. Length, sterile zone: About 2.1 cm. Length, female flower zone: About 1.3 cm. Diameter, male flower zone: About 9 mm. Diameter, sterile flower zone: About 5.5 mm. Diameter, female flower zone: About 8 mm. Shape: Columnar, spindle-shaped. Apex: Acute. Base: Obtuse. Aspect: Upright. Color, mature, male zone: Close to 155C tinged with close to 145C to 145D. Color, mature, sterile zone: Close to 155B. Color, mature, female zone: Close to 155B. Male flowers: Quantity per spadix: About 130. Shape: Obovate. Height: About 2.5 mm. Diameter: About 2.8 mm. Pollen amount: Moderate. Pollen color: Close to 9D. Female flowers: Quantity per spadix: About 76. Shape: Obovate. Height: About 2 mm. Diameter: About 2 mm. Stigma color: Close to 155B. Ovary color: Close to 155B.

*Scape*.—Length: About 27.2 cm. Diameter: About 6 mm. Strength: Sturdy; flexible. Aspect: Mostly erect. Texture and luster: Smooth, glabrous; dull sheen. Color: Close to 199D variably tinged with close to 182D and 147C, lightly stippled, streaked and tessellated with close to 147B to 147C and tinged with close to 200D and 199A; distally, close to 147C tinged with close to 199A, faintly and variably stippled, streaked and tessellated with close to 147C tinged with close to 199B.

*Seeds and fruits*.—To date, seed and fruit development have not been observed on plants of the new *Caladium*.

Disease & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Caribbean Coral' as illustrated and described.

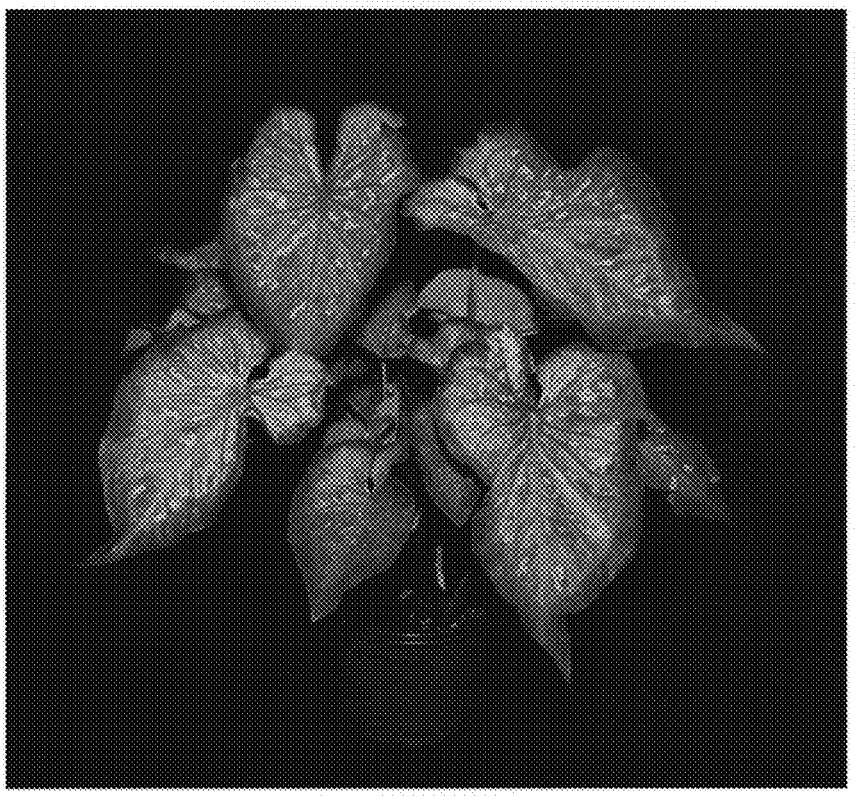

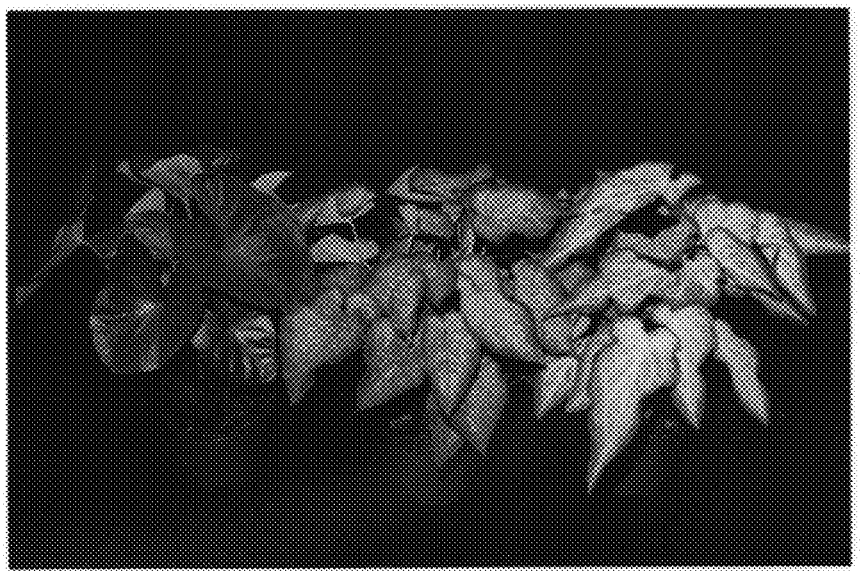
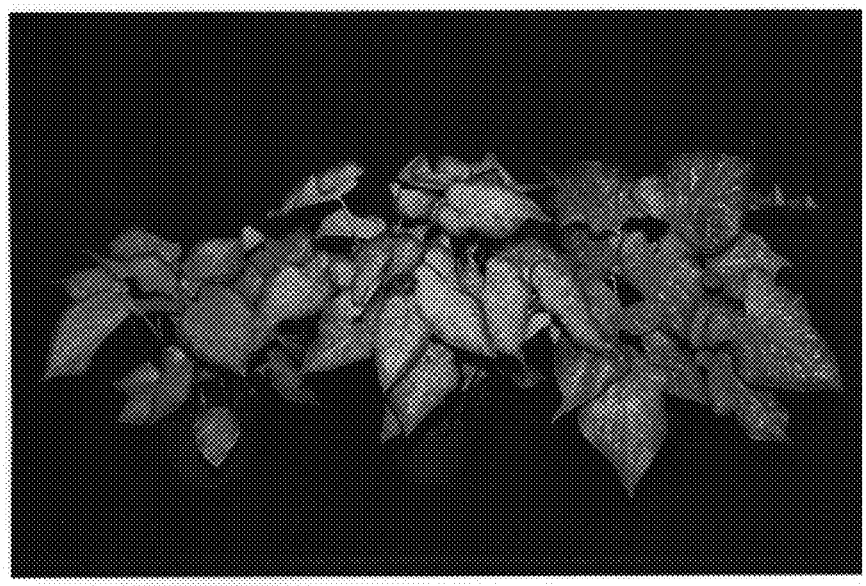

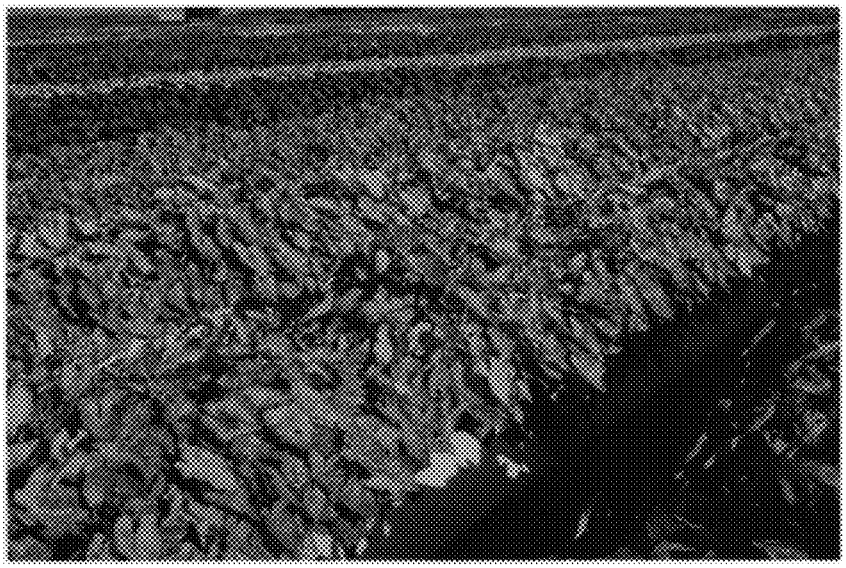
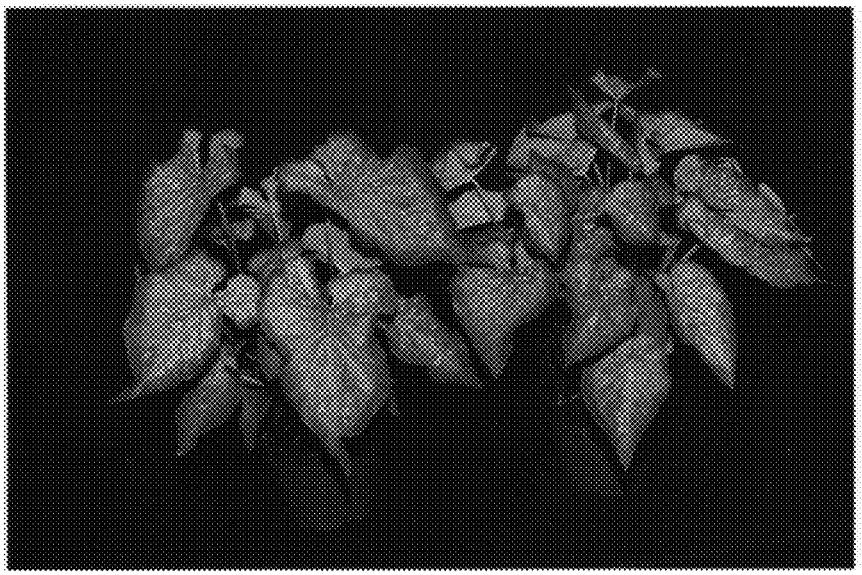

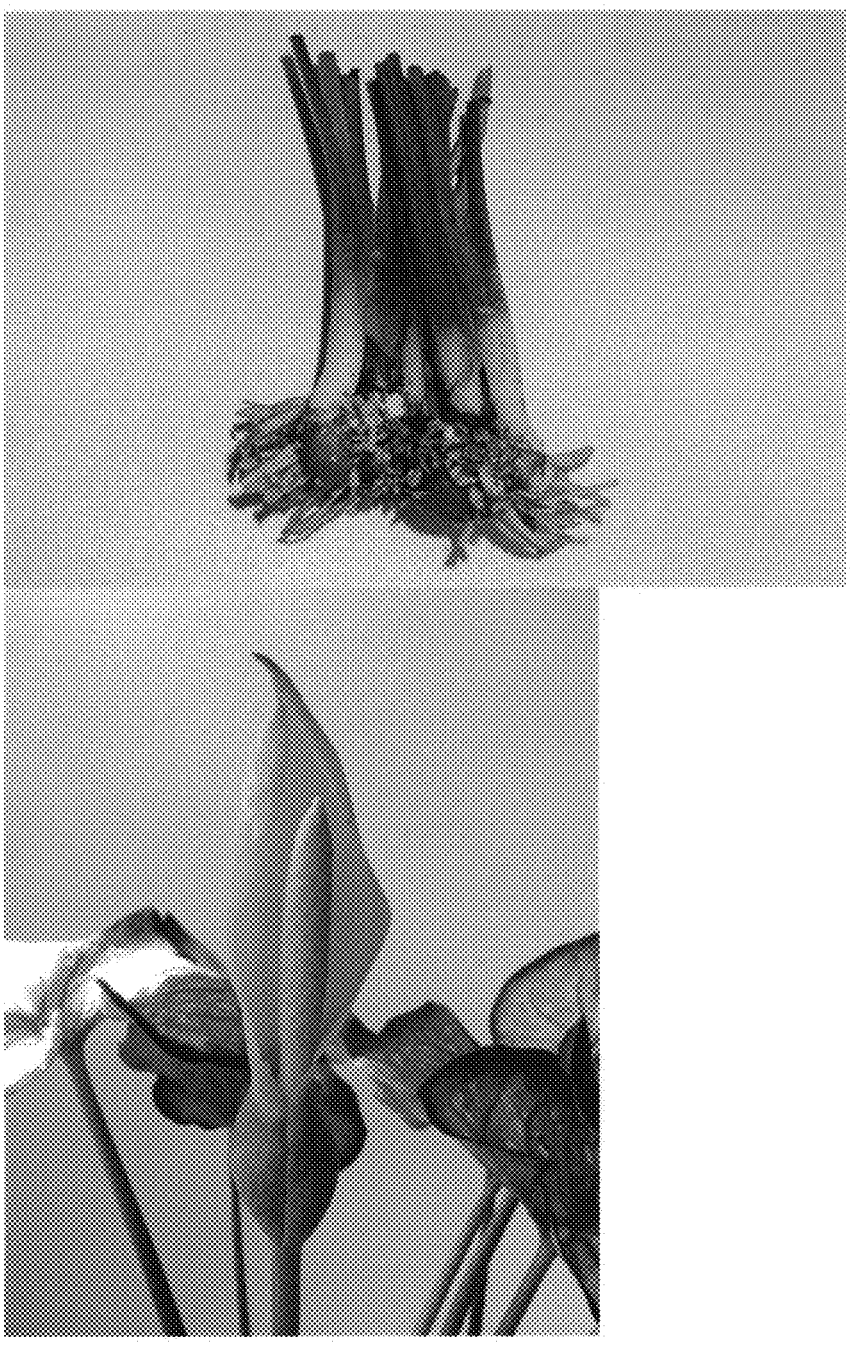

* * * * *